Figure 1:
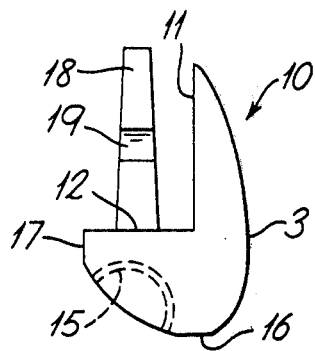
Figure 2:
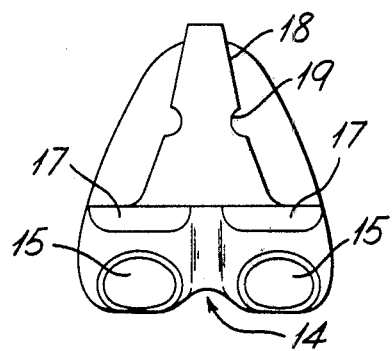
Figure 3:
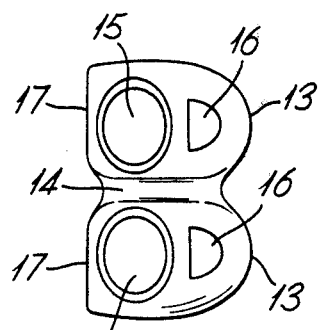
Figure 4:
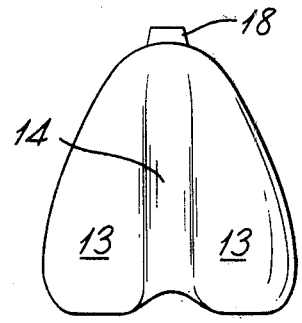

United States Patent [19]

Scales et al.

[11] 4,257,128
[45] Mar. 24, 1981

[54] ENDOPROSTHETIC KNEE JOINT

[75] Inventors: John T. Scales, Stanmore; Keith W. J. Wright, Ruislip, both of England

[73] Assignee: National Research Development Corporation, London, England

[21] Appl. No.: 37,514

[22] Filed: May 9, 1979

[30] Foreign Application Priority Data

May 12, 1978 [GB] United Kingdom ............... 19225/78

[51] Int. Cl.³ .............................................. A61F 1/03
[52] U.S. Cl. ................................... 3/1.911; 128/92 C
[58] Field of Search ......................... 3/1.9, 1.91, 1.911, 3/1.912, 1.913; 128/92 C

[56] References Cited

U.S. PATENT DOCUMENTS

| | | | |
|---|---|---|---|
| 3,506,982 | 4/1970 | Steffee | 128/92 C X |
| 3,694,821 | 10/1972 | Moritz | 3/1.911 |
| 3,795,922 | 3/1974 | Herbert et al. | 3/1.911 |
| 3,824,630 | 7/1974 | Johnston | 3/1.911 |
| 3,939,496 | 2/1976 | Ling et al. | 128/92 C X |
| 3,979,778 | 9/1976 | Stroot | 128/92 C X |
| 4,001,896 | 1/1977 | Arkangel | 3/1.91 |
| 4,094,017 | 6/1978 | Matthews et al. | 128/92 C X |

FOREIGN PATENT DOCUMENTS 2531080 2/1976 Fed. Rep. of Germany ............ 3/1.911
2501128 7/1976 Fed. Rep. of Germany ............ 3/1.911

*Primary Examiner*—Clifford D. Crowder
*Attorney, Agent, or Firm*—Cushman, Darby & Cushman

[57] ABSTRACT

An endoprosthetic knee joint device has femoral and tibial components respectively adapted for connection to the femur and tibia, and respective bearing surfaces for mutual articulatory engagement to simulate natural joint movements. It is now proposed that the femoral component has two transversely spaced sockets as bearing surfaces, and that the tibial component has two upstanding ball parts for respective articulation in the sockets. The ball parts can be separable, by the provision of stems engageable in apertures in the base part. Preferably, the sockets are enlarged relative to the balls to allow mutual rotation about the axis of the leg. Also, the sockets and balls can be of different material from their respective base parts, the latter suitably being of metal.

6 Claims, 6 Drawing Figures

ENDOPROSTHETIC KNEE JOINT

This invention concerns endoprosthetic joint devices and more particularly such devices for the knee joint.

Endoprosthetic knee joint devices in current clinical use can be broadly classified into two kinds. One kind is that of constrained devices which include two components for respective securement to the femur and tibia, with these components being mechanically interconnected in a hinge assembly. This kind of device is inherently stable and is commonly used to improve severe knee conditions, but has certain functional limitations. The other kind of device is that of unconstrained form in which the femoral and tibial components are held in mutual articulatory engagement by the natural capsule of the joint. This second kind of device is normally used in less severe conditions and can simulate normal knee function to a greater extent.

The present invention concerns the second kind of device just discussed and arises from the fact that such devices usually simulate the normal joint by the respective provisions of convex and concave articulatory surfaces on the femoral and tibial components. This simulation, however, is prospectively disadvantageous in that any debris resulting from wear or other causes can fall into the concave formation of the tibial component. Clearly if debris becomes trapped in this way between the articulating surfaces of the device, accelerated wear and other difficulties can occur.

The present invention accordingly comtemplates a reversal of the usual articulatory geometry in an unconstrained endoprosthetic knee joint device and more particularly proposes such a device comprising: a femoral component adapted on one side thereof for securement to the femur and formed on the opposite side thereof with two transversely spaced sockets; and a tibial component including a base part adapted on one side thereof for securement to the tibia, and two ball parts connectable to said base part projecting on the opposite side thereof from the tibia, said ball parts being respectively engageable in said sockets for mutual articulation therebetween.

Preferably the ball parts are separably connectable to the base part. Also it is preferred that such connection involve the provision of two transversely spaced apertures in the base part, and ball parts with stems engageable in such apertures.

It will be noted that the presently proposed device involves a double articulatory engagement which simulates the bicondylar nature of the natural knee joint, and in addition that the tibial component can be of a multi-part construction whereby the ball parts can be readily located at different heights from their base part. This allows the joint ligaments to be suitably tensioned and also, if appropriate, for correction of varus and valgus deformities.

In addition the form of construction just mentioned facilities the use of different combinations of materials in manufacture of the device. For example, the main body of the femoral component and the base part of the tibial component can each be made of an inherently stable material such as metal. The socket portions of the femoral components can be of metal, ceramic or plastics material, and the ball parts can be of metal or ceramic material, with the relevant choice of a combination of these materials being made with a view to minimising the friction therebetween and enhancing other properties. In fact particular interest presently lies in the use of ceramic material for the articulatory portions of the components.

The multi-part construction of the tibial component also facilitates replacement of the ball parts to take account of wear without necessitating the separation of securements to bone, and a corresponding construction for the femoral components can have the same advantage in respect of the sockets.

Figure 5:
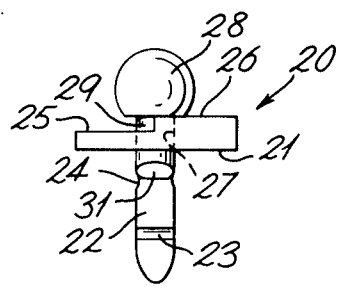
Figure 6:
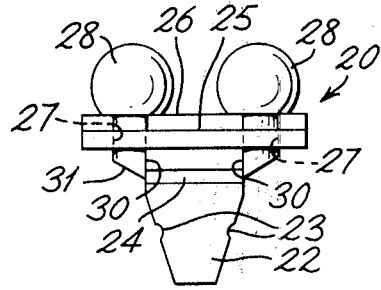

In order that the above and other aspects of the invention may be more clearly and fully understood, the same will now be described by way of example with reference to the accompanying drawings in which:

FIGS. 1 to 4 respectively diagrammatically illustrate the femoral component of one embodiment of the invention in side, rear, underneath plan, and front views, and FIGS. 5 and 6 similarly illustrate the tibial component of such embodiment in side and rear views.

The illustrated femoral component comprises a body 10 of generally L-shaped as seen in side view. The inner surface relative to such shape is in fact substantially L-shaped with two mutually angled faces 11 and 12. The outer surface is curved and shaped generally like the natural femoral condyles and so defines two convex rib faces 13 with a groove 14 extending therebetween. However, unlike the natural condyles, the outer surface is formed with two sockets 15 respectively located in the lower end portions of the ribs 13. In addition, each rib 13 is formed with two flats 16 and 17 respectively located adjacent opposite sides of the socket 15 along the rib.

The remaining part of the femoral component is a tapered blade 18 projecting from the face 12 in substantially parallel disposition to the adjacent face 11. The blade 18 is tapered in width, and has notches 19 in its longitudinal edges.

The illustrated tibial component comprises a base part including a platform 20 from one main surface 21 of which projects a tapered blade 22. The platform is of generally rectangular shape in plane view, but with rounded ends of corners, and the blade is located centrally along the major dimension of the platform as shown. The blade tapers in width, has notches 23 in its longitudinal edges, and has grooves 24 transversely across its side faces. The other main surface 25 of the platform 20 is stepped to provide an elevated portion 26 along one longitudinal side portion. The platform is, in addition, formed with two apertures 27 in the form of parallel bores which pass therethrough adjacent respective edges of the blade 22.

The tibial component comprises two further parts which each include a ball 28 from which a stem 29 projects. The stems are complementary with the apertures 27 for receipt therethrough with the ball uppermost, and each stem has a flat 30 on its longitudinal face to slidably engage the adjacent edge of the blade. The end face 31 of each stem is inclined and tapers in corresponding manner to the adjacent edge of the blade when located as just described.

In use of the illustrated embodiment the femur and tibia are suitably shaped and prepared for securement of the respective components thereto with use of bone cement. More particularly, the femoral component is located with its ribs 13 in place of the natural condyles and the faces 11 and 12 adjacent to the bone, with the blade penetrating the bone to key with cement in securement with the femur. The tibial component is similarly secured to the tibia with cement, with the platform located in place of the condyles and the blade penetrating the bone to key with the cement.

In function the stems are received in the platform, and the balls engage in the sockets to allow articulation. The flats 16 partway along the ribs 13 engage the elevated portion 26 to limit extension, and the flats 17 at the ends of the ribs engage the other portion of the platform surface 25 to limit flexion during articulation. The groove 14 engages and tracks the patella, or a prosthetic patellar device, during articulation. The flats 30 on the stems 29 engage the blade 22 to inhibit rotation of the balls.

While the invention has been described with more particular reference to the illustrated embodiment, it is not intended to be limited thereby but is capable of variation. For example, at present the balls and sockets are part-spherically shaped with the socket diameter being slightly larger than that of the balls to allow a small degree of rotation of up to about 10° between the components about the longitudinal axis of the leg. However a similar result is possible by the use of spheroidal shape for the sockets, and possibly the balls also, with the elongation of such shaping in the direction of the ribs. The balls can seat on the platform or they can be individually adjusted in height by the interposition of washers of selected thickness around the stems. As an alternative, a range of ball parts can be provided to give different heights. Another area for variation is in that of the blades which penetrate the bones and provide a cement key. Stems or other configurations can be provided for this purpose—indeed the use of cement itself is not an essential feature of the invention. Yet another area for variation is in that of choice of materials as discussed in the introductory passages above and it is to be noted that the femoral component can have replaceable socket parts fixed therein.

We claim:

1. An endoprosthetic knee joint device comprising: a femoral component adapted on one side thereof for securement to the femur and formed on the opposite side thereof with two transversely spaced sockets; a tibial component including a base part adapted on one side thereof for securement to the tibia and formed with two transversely spaced apertures, two ball parts each having a ball and a stem projecting therefrom, said stems being separately and removably engageable in a respective one of said apertures on said base part from the side of said base part opposite to said one side thereof, said balls being in respective mutual articulatory engagement with said sockets.

2. A device according to claim 1 wherein said sockets are enlarged relative to said balls to allow mutual articulation between said components about an axis passing successively through said components.

3. A device according to claim 2 wherein said sockets and balls are each spherically shaped, but said sockets are of lesser curvature than said balls.

4. A device according to claim 2 wherein said balls are spherically shaped, and said sockets are spheroidally shaped with similarly directed elongation.

5. A device according to claim 1 wherein said femoral component is of one material except for socket portions therein of a different material.

6. A device according to claim 5 wherein said tibial component comprises a base part of one material, and ball parts of which at least the balls thereof are of a different material.

* * * * *